United States Patent
Lathrop

[19]

[11] Patent Number: 6,083,250
[45] Date of Patent: Jul. 4, 2000

[54] APPARATUS AND METHOD FOR INHIBITING LESION FORMATION BY SELECTIVELY TREATING THE PRODROMAL STAGE OF THE LESION WITH A PULSATILE ELECTRICAL STIMULATION

[75] Inventor: Peter H. Lathrop, San Diego, Calif.

[73] Assignee: NexMed, Inc., Robbinsville, N.J.

[21] Appl. No.: 08/967,471

[22] Filed: Nov. 11, 1997

(Under 37 CFR 1.47)

Related U.S. Application Data

[63] Continuation-in-part of application No. 08/633,623, Apr. 17, 1996, abandoned, which is a continuation-in-part of application No. 08/545,945, Oct. 20, 1995, Pat. No. 5,607,461.

[51] Int. Cl.[7] .................................................. A61N 1/32
[52] U.S. Cl. ............................................................ 607/50
[58] Field of Search ................................ 607/2, 46, 50

[56] References Cited

U.S. PATENT DOCUMENTS

| | | | |
|---|---|---|---|
| 4,541,432 | 9/1985 | Molina-Negro et al. ............... | 607/46 |
| 4,895,154 | 1/1990 | Bartelt et al. .......................... | 607/50 |
| 4,913,148 | 4/1990 | Diethelm . | |
| 4,924,880 | 5/1990 | O'Neill et al. ......................... | 607/76 |
| 5,131,389 | 7/1992 | Giordani ................................ | 607/76 |
| 5,133,352 | 7/1992 | Lathrop et al. ........................ | 607/50 |
| 5,470,349 | 11/1995 | Kleditsch et al. ..................... | 607/150 |

*Primary Examiner*—William E. Kamm
*Assistant Examiner*—George R. Evanisko
*Attorney, Agent, or Firm*—J. Winslow Young

[57] ABSTRACT

An apparatus and method for preventing the formation of a herpes lesion by applying an electrical stimulation to the prodromal herpes lesion. The electrical stimulation apparatus is configured to be small enough to be hand portable and, preferably, concealable within the hand to accommodate treating the prodromal lesion at the onset of the formation of the prodromal lesion at any time and under any circumstance. The electrical stimulation is applied as an alternating current having a frequency range between one and 600 Hz. The alternating current is supplied with one of a square wave, a modified biphasic square wave, or a sine wave and between one and 100 milliamperes for a period of time up to 20 seconds.

7 Claims, 1 Drawing Sheet

APPARATUS AND METHOD FOR INHIBITING LESION FORMATION BY SELECTIVELY TREATING THE PRODROMAL STAGE OF THE LESION WITH A PULSATILE ELECTRICAL STIMULATION

RELATED APPLICATIONS

This patent application is a continuation-in-part patent application of my patent application Ser. No. 08/633,623 filed Apr. 17, 1996 now abandoned for APPARATUS AND METHOD FOR SELECTIVELY TREATING TISSUE WITH A PULSATILE ELECTRICAL STIMULATION which is a continuation-in-part patent application of Pat. application Ser. No. 08/545,945 filed Oct. 20, 1995 for APPARATUS AND METHOD FOR DELIVERING ELECTRICAL STIMULUS TO TISSUE now U.S. Pat. No. 5,607,461 issued Mar. 4, 1997.

BACKGROUND

1. Field of the Invention

This invention relates to the prevention of the formation of a herpes lesion and, more particularly, to a novel apparatus and method for the selectively controlled delivery of electrical stimulation to the tissue during the prodromal stage of the herpes lesion to thereby prevent the subsequent formation of the herpes lesion.

2. The Prior Art

Various systems have been devised for delivering electrical stimulation to living tissue for the purpose of treating a condition involving that living tissue. For example, U.S. Pat. No. 5,117,826 teaches a device for the combined nerve fiber treatment and body stimulation while U.S. Pat. No. 5,133,352 teaches a method for treating herpes simplex. A small size, low frequency curing apparatus is shown in U.S. Pat. No. 4,922,906. An electrotherapeutic treatment apparatus is shown in U.S. Pat. No. 5,107,835. U.S. Pat. No. 4,913,148 discloses the treatment of herpes simplex I and II as well as herpes zoster. A low frequency electrotherapeutic device is disclosed in U.S. Pat. No. 5,133,351.

The need for an effective treatment of skin lesions caused, for example, by the herpes virus is amply demonstrated by the fact that nearly 100 million American citizens are affected by the virus in at least one of its two forms, Herpes Simplex I and Herpes Simplex II. Herpes Simplex I is customarily associated with herpes virus infections above the waist, primarily in and around the mouth, while Herpes Simplex II accounts for a high percentage of the genital infections. In both instances of infection the physical manifestation of the occurrence of a lesion is signalled by a tingling or burning sensation at the lesion site at least 24 to 48 hours prior to an actual outbreak of the lesion in the tissue. This tingling sensation is accompanied by an increased reddening of the tissue followed by the appearance of vesicles which subsequently break and form a crust. This developmental stage of lesion development is referred to as the prodromal stage. Unless the lesion becomes infected with a secondary infection the skin will clear and appear normal again within about eight to fourteen days from the onset of the lesion formation.

Various treatment protocols have been developed for the topical treatment of herpes virus lesions, particularly those lesions associated with Herpes Simplex II. These include the use of drying agents such as alcohol, spirits of camphor, and ether, or ointments, cremes, topical anesthetics, and antiseptic solutions. Other topical agents that include Idoxuridine, Trifluorothymidine, or Acyclovir have been found to be somewhat effective. However, at present, all of these treatment modalities have been shown to be only marginally effective against the disease, much to the extreme discomfort of the patient. Further, many of these chemical treatment modalities are accompanied by potentially serious side effects.

However, and perhaps, more importantly, all these treatment modalities involve treating the herpes lesion after it has formed. As anyone who has ever been the victim of a herpes lesion knows, the presence of the lesion itself is most disconcerting. Not only is the lesion uncomfortable due to the pain associated with the lesion but probably the most difficult aspect is the visible presence of the lesion. Customarily, the lesion forms around the mouth and nose of the victim and is most unsightly in its appearance.

In view of the foregoing, it would be an advancement in the art to provide a safe and effective treatment apparatus and method for preventing the formation of a herpes lesion. It would be an even further advancement in the art to treat the lesion site in its prodromal state thereby preventing the formation of a lesion. Another advancement in the art would be to apply electrical stimulation to the lesion site within 24 to 48 hours prior to the appearance of the lesion. An even further advancement in the art would be to apply the electrical stimulation to the lesion site as a pulsatile waveform to more effectively interrupt the viral infection at the lesion site. It would be an even further advancement in the art to provide an apparatus and method for enabling the patient to treat the infection in its prodromal state. Such a novel apparatus and method is disclosed and claimed herein.

BRIEF SUMMARY AND OBJECTS OF THE INVENTION

The present invention is a novel apparatus and method for preventing the formation of a herpes lesion by treating it in its prodromal stage so that the legion will never appear. The treatment is accomplished using electrical stimulation which is delivered as a preselected pulsatile electrical stimulation for a preselected period of treatment time. The electrical stimulation apparatus is configured as a hand-held, battery powered unit having a controller and a pulse generator for delivering the predetermined quantity and type of electrical energy to the incipient lesion during its prodromal stage.

It is, therefore, a primary object of this invention to provide improvements in treating herpes lesions.

Another object of this invention is to provide improvements in the method of preventing the formation of a herpes lesion.

Another object of this invention is to provide an electrical stimulation apparatus for delivering a pulsatile electrical stimulation to an incipient herpes lesion during its prodromal stage.

Another object of this invention is to provide a controller for controlling the pulsatile electrical stimulation delivered to the pre or post lesion site.

These and other objects and features of the present invention will become more readily apparent from the following description taken in conjunction with the appended claims.

DETAILED DESCRIPTION OF THE PREFERRED EMBODIMENT

Figure 1:
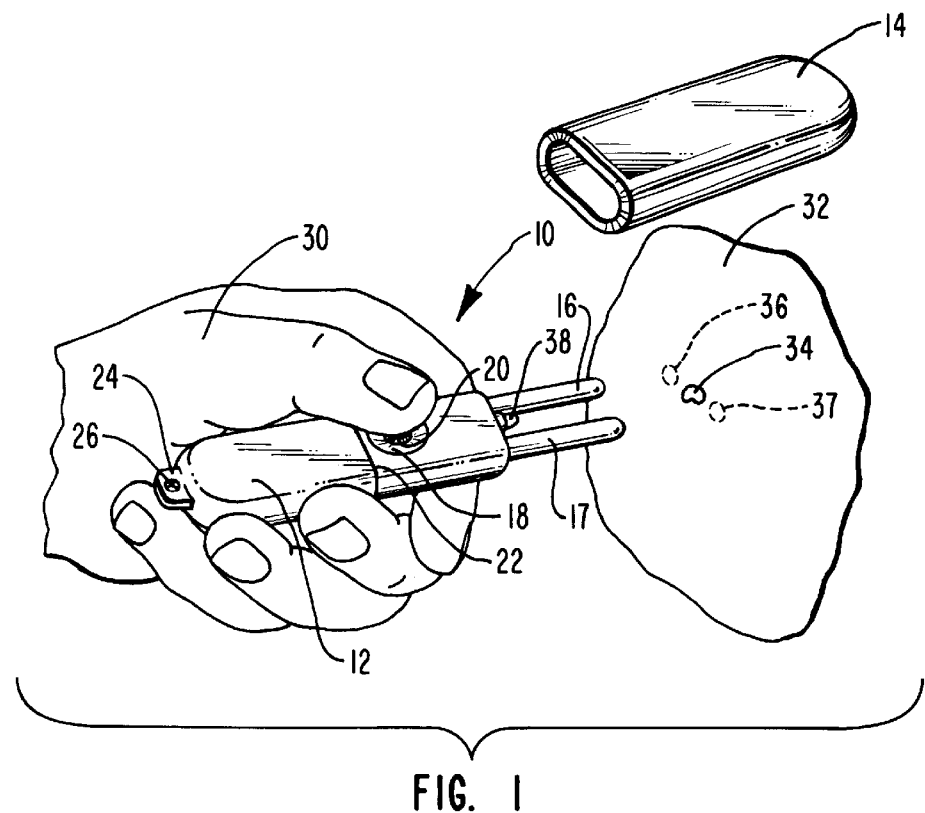
FIG. 1 is a perspective view of one presently preferred embodiment of my novel electrical stimulation apparatus shown in the environment of a hand and a lesion.

The invention is best understood from the following description with reference to the drawing wherein like parts are designated by like numerals throughout.

General Discussion

I have discovered that I can prevent the formation of the external manifestation of a herpes lesion by treating the incipient lesion with an electrical stimulation during the prodromal stage of the lesion. This prodromal stage is readily evident to the patient due to the tingling sensation one feels approximately twenty-four to forty-eight hours before the lesion erupts into a full-blown herpes lesion. Advantageously, I have found that it is essential to have an electrical stimulation apparatus that is sufficiently small so as to be hand portable, and more importantly, of a suitably small size so as to enable the patient to discretely treat the prodromal lesion at any time and under practically any circumstance.

Accordingly, I have configured my novel electrical stimulation apparatus invention as a hand-portable device. A battery provides the necessary electrical energy for the electrical stimulation. An electrical circuit is included inside the device and is designed to selectively change the direct current electrical energy from the battery to an alternating current having a predetermined characteristic suitable for treatment of the lesion during its prodromal stage. The battery and electrical circuit are contained within a housing. A pair of small, cylindrical, probe-type electrodes extend from the housing. A cap is designed to enclose the electrodes and engage the corresponding end of the housing in a snap fit relationship. A switch is also provided on the surface of the housing at a location where it is enclosed by the cap so that it is only accessible when the cap is removed. A treatment LED (Light Emitting Diode) is mounted to the housing between the electrodes and provides a visible indication to the user when electrical energy is being supplied to the electrodes. The entire device is specifically configured to be of such a relatively small size that it can easily fit within the palm of a user's hand.

DETAILED DESCRIPTION

Referring now to FIG. 1, a herpes lesion is illustrated schematically in its prodromal stage at 34 on tissue 32. Prodromal lesion 34 is not visible but is illustrated as a distinct area for purposes of understanding my novel discovery. In reality, prodromal lesion 34 is invisible to the eye and its presence only known due to the customary tingling sensation felt in tissue 32. It is during this unseen, but tactilely sensed stage, for prodromal lesion 34 that I am able to successfully treat prodromal lesion 34 to prevent it from erupting into a visibly noticeable lesion (not shown). It is for this very important reason that I have created my novel discovery.

The novel electrical stimulation apparatus of this invention is shown generally at 10 held in a hand 30. Electrical stimulation apparatus 10 includes a housing 12 with a closure 14 configured as a cap that can be releasably mounted to housing 12. A pair of electrodes 16 and 17 extend from housing 12 and are enclosed within the confines of closure 14 when closure 14 is mounted to housing 12. Housing 12 includes a recessed section 22 formed adjacent electrodes 16 and 17 so that closure 14 is telescopically received in recessed section 22 thereby presenting electrical stimulation apparatus 10 with a smooth, external profile. A switch 20 is mounted to housing 12 within recessed section 22 and is surrounded by a recess 18 which allows switch 20 to have a top surface that is coplanar with recessed section 22 and to simultaneously allow switch 22 to be depressed by one of the fingers of hand 30. The end of housing 12 includes a tab 24 having a hole 26 therethrough for the purpose of providing an attachment site for the attachment of electrical stimulation apparatus 10 to a keychain, or the like (not shown) for ease of retention and retrieval.

Advantageously, electrical stimulation apparatus 10 is of such a small size relative to hand 30 that it can be easily concealed within the confines of hand 30. This means that the user (hand 30) is able to discretely retrieve electrical stimulation apparatus 10 from a pocket, key chain, or the like (not shown) and apply its electrical stimulation to prodromal lesion 34 regardless of the location or activity of the user.

Treatment is commenced by the user (hand 30) removing closure 14 from electrical stimulation apparatus 10 and pressing the tips of electrodes 16 and 17 against tissue 32 so as to bracket prodromal lesion 34 as shown schematically by contact points 36 and 37. Upon pressing the tips of electrodes 16 and 17 against tissue 32 the user simply presses switch 20 to activate circuit 40 (FIG. 2) to commence the treatment cycle of electrical stimulation apparatus 10. A treatment LED (Light Emitting Diode) 38 provides a visual indication that circuit 40 is operational and remains illuminated as long as circuit 40 is operational. This feature is specifically designed to encourage the user to hold electrodes 16 and 17 against tissue 32 and in a bracketing relationship across prodromal lesion 34 during the entire treatment cycle. This is important because the electrical energy applied to tissue 32 by electrodes 16 and 17 is of such low power as to not be felt by the user. Otherwise, the user may not hold electrodes 16 and 17 against tissue 32.

Figure 2:
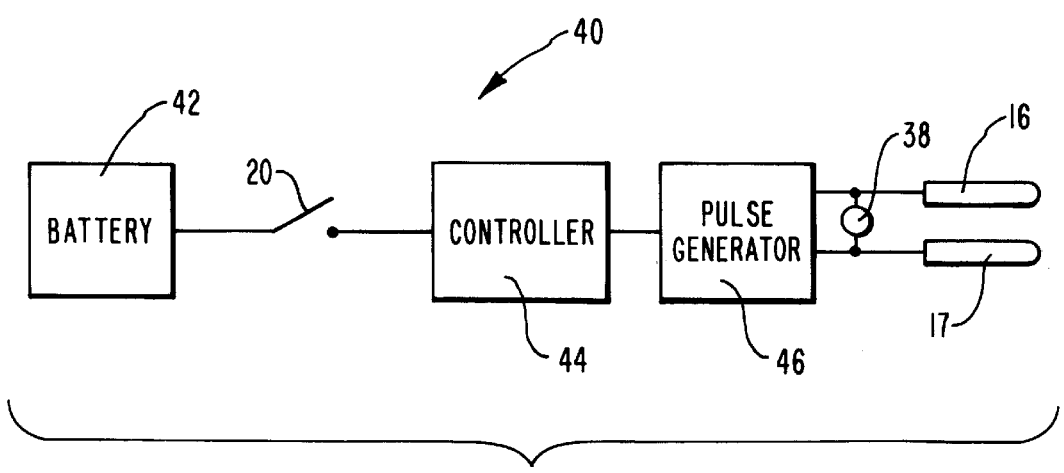
FIG. 2 is a schematic diagram of the circuitry of the novel electrical stimulation apparatus of FIG. 1.

Referring now also to FIG. 2, the electrical circuit of my novel electrical stimulation apparatus 10 is shown generally at 40 and includes a battery 42, a controller 44, and a pulse generator 46 along with switch 20, electrodes 16 and 17, and treatment LED 38. In the presently preferred embodiment of this invention battery 42 is a conventional 9 volt battery. Controller 44 provides several functions: first, it controls the direction of the current flow through electrodes 16 and 17; second, it controls the duration of the particular flow of current; third, it controls the total treatment period initiated when switch 20 is closed (as reflected by the duration of illumination of treatment LED 38); and, fourth, it controls the total amperage of the current delivered to pulse generator 46.

Pulse generator 46 processes the incoming electrical energy from controller 44 and forms the electrical energy into pulses that alternate in the direction of the current flow so as to create, in effect, an alternating current that is then delivered to electrodes 16 and 17 and thereby provide treatment to prodromal lesion 34 through electrical stimulation. Specifically, controller 44 and pulse generator 46 are configured to deliver current of 9, 18, or 27 milliamperes alternating current at zero ohms resistance with a frequency of one to 600 Hz although preferably a frequency 1, 2, or 10 Hz. The pulse can have a square wave, a modified biphasic square wave, or be delivered to electrodes 16 and 17 as a sine wave.

One very important aspect of this invention is that the level of electrical energy is significantly lower than that used for anesthesia purposes (as taught by O'Neill et al. U.S. Pat. No. 4,924,880, for example) or even transcutaneous nerve stimulation purposes as taught by many others. In fact, my invention uses such a small amount of electrical energy as to not be sensed at all which is why I included LED 38 as a means for signalling to the user that electrical energy is being supplied to electrodes 16 and 17.

The Method

The method of this invention includes forming a housing 12, preferably of a sufficiently reduced size to provide electrical stimulation apparatus 10 as a hand-portable device. Battery 42, controller 44, and pulse generator 46 are mounted inside housing 12 to complete electrical circuit 40 which also includes switch 20, treatment LED 38, and electrodes 16 and 17. Closure 14 is prepared for enclosing electrodes 16 and 17 and is configured for being releasably mounted to recessed section 22 on the end of housing 12 in a snap fit relationship. Removal of closure 14 not only exposes electrodes 16 and 17 but also exposes switch 20 and treatment LED 38.

The use of electrical stimulation apparatus 10 is commenced by removing closure 14 and touching the tips of electrodes 16 and 17 to tissue 32 so as to bracket prodromal lesion 34 as represented by contact points 36 and 37. Switch 20 is then pressed to cause electrical energy to flow from battery 42 to controller 44 and pulse generator 46 to electrodes 16 and 17. Controller 44 is preprogrammed with the particular treatment protocol both as to duration and the amount of electrical energy directed to electrodes 16 and 17. Pulse generator 46, on the other hand, converts the electrical energy from controller 44 into an alternating-type current in that it periodically switches the direction of current flow for electrodes 16 and 17.

In this presently preferred embodiment of electrical stimulation apparatus 10 the electrical current delivered to electrodes 16 and 17 or, more particularly, to contact points 36 and 37 is delivered as 1, 2, or 10 Hz frequency square wave, a modified biphasic square wave, or a sine wave at an amperage within the range of about one to 100 milliamperes, preferably in steps of 9, 18, or 27 milliamperes. The total treatment time found efficacious is only about 20 seconds.

Accordingly, the user is readily enabled through the use of electrical stimulation apparatus 10 prevent the visible manifestation of a herpes lesion by suitably applying electrical stimulation apparatus 10 to prodromal lesion 34. further, since one can never predict when one will experience the tactile sensation exhibited by prodromal lesion 34, it is essential that electrical stimulation apparatus 10 be configured as a small, hand-portable device, preferably, one that is easily concealable within the confines of hand 30. For example, if the user were enjoying an intimate dinner with a friend and sensed the onset of the tingling sensation that signals the presence of prodromal lesion 34, the user is readily able to prevent the subsequent formation of a visible herpes lesion by the use of my novel electrical stimulation apparatus 10.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for preventing a herpes lesion by delivering electrical stimulation to prodromal lesion comprising the steps of:

preparing an electrical circuit by electrically interconnecting a battery, a controller, a pulse generator, a pair of electrodes, and a control switch;

making said electrical circuit hand portable by enclosing said electrical circuit in a hand-portable housing with said electrodes extending outwardly from said housing;

bringing said hand-portable housing into proximity with the prodromal lesion so as to accommodate stimulating the prodromal lesion with electrical energy alternating current supplied by said pulse generator by pressing said electrodes adjacent the prodromal lesion; and stimulating the prodromal lesion with said alternating current by closing said switch thereby directing said alternating current from said battery through said controller and said pulse generator to said electrodes.

2. The method defined in claim 1 wherein said stimulating step includes delivering said alternating current as a frequency within the range of approximately one to ten Hz.

3. The method defined in claim 2 wherein said alternating current is a square wave.

4. The method defined in claim 2 wherein said alternating current is a sine wave.

5. The method defined in claim 2 wherein said alternating current is a modified biphasic square wave.

6. The method defined in claim 2 wherein said stimulating step includes delivering said electrical energy as a current having an amperage within the range on the order of about one to 100 milliamperes.

7. A method of preventing a herpes simplex lesion by treating the prodromal lesion with an apparatus having two electrodes extending from a hand-portable housing, said housing including a battery operable to provide electrical energy and an electrical circuit operable to deliver said electrical energy as AC electrical energy to said electrodes, said electrical circuit including a switch to control delivery of said electrical energy from said battery to said electrical circuit, said method comprising the steps of:

pressing said electrodes adjacent the prodromal lesion; and activating said electrical circuit with said switch causing said AC electrical energy to flow to said electrodes and to treat said prodromal lesion thereby preventing said herpes simplex lesion.

* * * * *